(12) United States Patent
Pierenkemper

(10) Patent No.: US 9,205,249 B2
(45) Date of Patent: Dec. 8, 2015

(54) APPARATUS FOR ELECTROSTIMULATION AND METHOD FOR CONTROLLING MULTIPLE ELECTRODES IN AN APPARATUS FOR ELECTROSTIMULATION

(71) Applicant: Pierenkemper GmbH, Ehringshausen (DE)

(72) Inventor: Roger Pierenkemper, Marburg (DE)

(73) Assignee: Pierenkemper GmbH, Ehringshausen (DE)

( * ) Notice: Subject to any disclaimer, the term of this patent is extended or adjusted under 35 U.S.C. 154(b) by 25 days.

(21) Appl. No.: 14/172,205

(22) Filed: Feb. 4, 2014

(65) Prior Publication Data
US 2015/0094788 A1   Apr. 2, 2015

(30) Foreign Application Priority Data

Oct. 2, 2013   (DE) .......................... 10 2013 110 984

(51) Int. Cl.
| A61N 1/04 | (2006.01) |
| A61F 7/00 | (2006.01) |
| A61N 1/36 | (2006.01) |

(52) U.S. Cl.
CPC ................ *A61N 1/0452* (2013.01); *A61F 7/00* (2013.01); *A61N 1/0476* (2013.01); *A61N 1/0492* (2013.01); *A61N 1/36014* (2013.01); *A61F 2007/0018* (2013.01)

(58) Field of Classification Search
None
See application file for complete search history.

(56) References Cited

U.S. PATENT DOCUMENTS

| 5,285,781 A | 2/1994 | Brodard |
| 7,072,721 B1 | 7/2006 | Trent |
| 8,145,318 B2 | 3/2012 | Van Herk |
| 8,255,060 B2 * | 8/2012 | Goetz et al. ..................... 607/59 |
| 2006/0206162 A1 * | 9/2006 | Wahlstrand et al. ............ 607/46 |
| 2010/0087903 A1 | 4/2010 | Van Herk et al. |
| 2010/0152794 A1 | 6/2010 | Radivojevic et al. |
| 2011/0015697 A1 | 1/2011 | McAdams |

(Continued)

FOREIGN PATENT DOCUMENTS

| DE | 691 28 213 T2 | 6/1998 |
| DE | 10 2009 013 627 A1 | 9/2010 |
| DE | 20 2011 109 226 U1 | 8/2012 |
| KR | 10-2012-0041525 A | 5/2012 |

OTHER PUBLICATIONS

German Search Report dated Jul. 23, 2014 in German Application No. 10 2013 110 984.5, with English translation of relevant parts.

(Continued)

*Primary Examiner* — Brian T Gedeon
(74) *Attorney, Agent, or Firm* — Collard & Roe, P.C.

(57) ABSTRACT

An apparatus for electrostimulation has a whole-body support and electrodes disposed in the support. The electrodes are disposed in pairs, relative to a center longitudinal axis of the apparatus, and are configured so that they can be controlled one after the other or simultaneously. A method for controlling multiple electrodes in an apparatus for electrostimulation disposes the electrodes in or on the apparatus for electrostimulation, which has a support for part of the body or for the whole body. The electrodes are configured so that they can be controlled one after the other or simultaneously. The electrodes are controlled individually or in pairs, with regard to a duration and/or an intensity of the stimulation.

28 Claims, 3 Drawing Sheets

(56) References Cited

U.S. PATENT DOCUMENTS

2011/0093030 A1 4/2011 Goetz et al.
2011/0264002 A1 10/2011 Kolen et al.

OTHER PUBLICATIONS

European Search Report of 14152769.7, dated Mar. 31, 2014, with English translation of relevant parts.

* cited by examiner

APPARATUS FOR ELECTROSTIMULATION AND METHOD FOR CONTROLLING MULTIPLE ELECTRODES IN AN APPARATUS FOR ELECTROSTIMULATION

CROSS REFERENCE TO RELATED APPLICATIONS

Applicant claims priority under 35 U.S.C. §119 of German Application No. 10 2013 110 984.5 filed Oct. 2, 2013, the disclosure of which is incorporated by reference.

BACKGROUND OF THE INVENTION

1. Field of the Invention

The invention relates to an apparatus for electrostimulation, having a support for part of the body or for the whole body, and electrodes disposed in the support. Furthermore, the invention relates to a method for controlling multiple electrodes in an apparatus for electrostimulation.

2. Description of the Related Art

Apparatuses for electrostimulation, which can be used locally, for example arm cuffs or leg cuffs, are known from practice.

From the Korean document KR 10-2012-0041525, mats are known that are configured as an apparatus for electrostimulation. The whole-body mats according to this prior art have electrodes that are disposed in the region of the body of a person to be treated. The electrodes are configured in line shape or point shape, thereby causing the disadvantage that electrostimulation of nerves or muscles is very restricted. Effective nerve or muscle stimulation is not possible with these electrodes configured in point shape or line shape, which are disposed in a mat configured to be planar.

Muscles and/or nerves can be stimulated with electrostimulation.

In the case of nerve stimulation, an electric field intensity having a sufficiently strong gradient is applied, which brings about triggering of an action potential in the nerve, which reaches the motor end plate of the addressed muscle, along the motor nerve, and there again triggers an action potential that subsequently brings about contraction of the muscle. Aside from motor nerves, sensitive nerves are also excited or exclusively excited.

In the case of direct muscle cell stimulation, a muscle cell is excited directly by means of electrical stimuli that are significantly greater and stronger than in the case of stimulation of nerves. In both cases, it is known to perform this electrostimulation using surface electrodes, by way of the skin.

Frequently, in the case of muscle stimulation, medium-frequency current is used, which works with frequencies of above 1,000 hertz (Hz), for example, so that the sensitive stress is clearly reduced, because the electrical resistance of the skin to an electrical stimulus is dependent on frequency, in an inverse proportion. Here, frequencies between 1,000 Hz and 10,000 Hz and modulated currents have proven to be particularly effective.

SUMMARY OF THE INVENTION

The technical problem on which the invention is based consists in indicating an apparatus and a method for electrostimulation with which clearly improved electrostimulation is possible.

This technical problem is solved by an apparatus having the characteristics according to one aspect of the invention and by a method having the characteristics according to another aspect of the invention.

The apparatus for electrostimulation according to the invention, having a support for part of the body or for the whole body, and electrodes disposed in the support, is characterized in that the electrodes are disposed in pairs, relative to a center longitudinal axis of the apparatus, that the electrodes are configured to be planar, and that electrode pairs that are formed from adjacent electrodes are configured so that they can be controlled one after the other or simultaneously.

Preferably, the apparatus according to the invention has a support for the back or is configured as a contact surface in the region of a back. However, it is also possible to configure the apparatus according to the invention for other regions of the body, for example for the arm or leg region.

The invention demonstrates the advantage that the electrodes are disposed in pairs relative to the center longitudinal axis. In this way, whole-body stimulation from the head to the feet or in the partial region of the body that is covered by the apparatus according to the invention, for example the back, is possible.

Both body halves to the right and left of the spinal column are stimulated as the result of the arrangement in pairs relative to the center longitudinal axis of an apparatus that is configured as a back support or a whole-body support.

Stimulation takes place by way of adjacent electrode pairs, so that a current flow between two adjacent electrodes, in each instance, is present. The adjacent electrode pairs can be selected to the right and left of the spinal column when the apparatus is configured as a back support. The possibility also exists of applying current to adjacent electrode pairs only to the left or right of the spinal column. The electrode pairs, which are formed from adjacent electrodes, can be controlled one after the other or simultaneously.

The apparatus according to the invention is furthermore characterized in that the electrode pairs can be controlled simultaneously or one after the other. In this way, it is possible to provide for wave-type stimulation of the body by means of wave-type powering up of the electrode pairs, for example.

It is advantageous if two electrodes, in each instance, are disposed in pairs relative to the center longitudinal axis of the apparatus. Because the electrodes are configured to be planar, they have a size that covers the region to be stimulated over a large area or even completely. In this connection, it is sufficient to provide one electrode, in each instance, on the two sides of the center longitudinal axis. In this way, the wiring effort in the apparatus and the effort with regard to control of the electrodes are significantly reduced. A significant advantage of the planar configuration of the electrodes is also that the electrodes touch the muscle regions to be stimulated with a greater surface area, and in this way more effective muscle stimulation is possible.

According to a further very advantageous embodiment of the invention, at least a part of the electrodes has a curved surface. Because the electrodes are configured to be planar, the formation with a curved surface is advantageous, because in this case, the electrodes can be adapted to the body contour. For example, the electrodes in the cervical vertebrae region can be configured to be convex, while they are advantageously configured to be concave in the lumbar vertebrae region.

According to another advantageous embodiment of the invention, at least a part of the electrodes is disposed inclined relative to a base surface of the support. In this way, as well, optimal adaptation of the electrodes to a body contour is possible.

It is advantageous if the apparatus is configured in such a manner that the curved surface of the electrodes is configured as a curved surface adapted to a body contour and/or that the inclination of the electrodes is configured as an inclination adapted to a body contour. In this way, the result is achieved that the electrodes lie against the body and thereby optimal electrostimulation is possible.

It is advantageous if at least six electrode pairs, particularly advantageously at least twelve electrode pairs are provided.

Wave-shaped stimulation is particularly well possible by means of the plurality of electrode pairs; this means that stimulation can start in the sacrum region and that stimulation can continue all the way to the cervical vertebrae region, by powering the electrode pairs up one after the other, if the mat is configured as a back support.

According to the invention, it is advantageous if it is provided that the electrode pairs are configured so that they can be powered up gradually and powered down again gradually, in each instance. This means that it is advantageous if a first electrode pair is powered up gradually and powered down again gradually. It is advantageous if the next subsequent electrode pair is powered up during the powering-down process of the first electrode pair, so that this pair powers up gradually, so that wave-type electrostimulation with the apparatus according to the invention is possible.

It is possible to allow the apparatus to run with merely one stimulation wave, in other words a first electrode pair is powered up gradually and powered down again gradually. During the powering-down process of the first electrode pair, the next subsequent adjacent electrode pair is configured to power up gradually. During this time, no other electrode pair is powered up or down.

The possibility also exists of performing electrostimulation in multiple waves simultaneously. In this connection, a first electrode pair and at least one other non-adjacent electrode pair is powered up gradually and subsequently powered down again gradually. Subsequently, the adjacent, subsequent electrode pair, in each instance, is powered up gradually and powered down again gradually, so that wave-type electrostimulation occurs.

It is advantageous if the stimulation is carried out with a current having a low frequency between 0 and 1,000 hertz (Hz) or a medium frequency between one and ten kilohertz (kHz). These frequency ranges are particularly advantageous for electrostimulation in the muscle region.

According to another advantageous embodiment of the invention, the apparatus is configured so that it can be heated. This increases the stimulation effect, because in this connection the muscles relax well and/or more quickly during stimulation.

According to another advantageous embodiment of the invention, the apparatus has a couch surface adapted to a body contour. In this way, too, the muscles relax particularly well and particularly quickly, so that electrostimulation is particularly effective.

According to another advantageous embodiment of the invention, the apparatus is formed from silicone. The use of silicone offers the advantage that for one thing, the electrodes can be embedded very well in the silicone. Furthermore, this material can be kept clean easily, so that the apparatus according to the invention also meets special hygiene regulations.

The silicone and the supports formed from it are soft and resilient, thereby in turn causing the relaxation effect to occur in clearly better and faster manner, and thereby increasing the degree of effectiveness of the electrostimulation.

According to a further advantageous embodiment of the invention, the apparatus has an interrupted couch surface.

In particular, the region along the center longitudinal axis is recessed. In this way, the spinal column region of the person using the apparatus is recessed with regard to the couch surface. Therefore there are also no electrodes disposed in this region, which is practical from a medical point of view. The recess along the center longitudinal axis is furthermore also practical with regard to a relaxed position of the user person, by means of increasing the stimulation effect. Furthermore, the person does not lie on the apparatus with his/her spinous processes, which would be uncomfortable or even painful. Furthermore, in this way it is guaranteed that the electrodes lie against the muscular part of the back, thereby making it possible to perform stimulation of the muscles in optimized manner.

The apparatus according to the invention, in the form of a back support, primarily serves for electrostimulation of the muscles of the back, without the osseous parts.

It is advantageous if the apparatus according to the invention has multiple individual supports, in other words the couch surface is divided into at least two individual supports transverse to the center longitudinal axis. The apparatus according to the invention can have a recess in the region of the center longitudinal axis and/or recesses transverse to the center longitudinal axis.

In this way, the mobility of the silicone support is increased, thereby in turn increasing the relaxation effect. Furthermore, in the embodiment with individual supports, the electrodes lie better against the body of the person, thereby increasing the stimulation effect.

It is advantageous if at least one electrode is disposed in each individual support. According to a particularly preferred embodiment of the invention, an electrode is disposed in each individual support, in each instance. Because the contact surfaces are advantageously configured to be movable, for example by means of being formed from silicone, the electrodes can optimally adapt to the body contour of the person lying on the apparatus, so that contact over the full area, if at all possible, and thereby optimal electrostimulation take place.

According to a particularly preferred embodiment of the invention, the electrodes are disposed, in each instance, bordering on the recess disposed in the center longitudinal axis. In this way, it is guaranteed that stimulation of the entire body or body region takes place, specifically in the region close to the center. It is advantageous if the electrodes are disposed at a distance from one another and/or electrically insulated from one another, so that electrostimulation takes place by means of current flow through the muscles.

It is advantageous if the electrodes have different sizes, at least in part, with regard to their contact surface. In this way, optimal stimulation in the different regions, for example the back, is possible. Thus, the electrodes are configured to be bigger in the region of the sacrum, with regard to their contact surface, than the electrodes in the shoulder region or in the region of the thoracic spinal column. It is advantageous if the electrodes in the region of the cervical spinal column have a lesser width but a greater length than the remaining electrodes. It is advantageous if the electrodes in the lumbar vertebrae region have the greatest width.

According to a further advantageous embodiment of the invention, the stimulation intensity of each electrode is individually adjustable. It is also possible to adjust the stimulation intensity of groups of electrodes. In this way, individual adaptation of the electrostimulation is possible, thereby making the stimulation very effective.

The method according to the invention, for controlling multiple electrodes in an apparatus for electrostimulation, in which the electrodes are disposed in or on the apparatus for electrostimulation, which has a support for part of the body or for the whole body, is characterized in that the electrodes are configured so that they can be controlled one after the other or simultaneously, and that the electrodes are controlled individually or in pairs, with regard to a duration and/or an intensity of the stimulation.

Individual powering up or powering up one after the other offers the advantage that individual stimulation programs can be created for each user.

It is advantageous if the electrodes or electrode pairs are controlled in wave form, one after the other, with regard to intensity. Wave-type control is advantageous for effective electrostimulation.

According to a further advantageous embodiment of the invention, the electrode pairs are powered up gradually and powered down again gradually, with regard to intensity. In this way, the wave-type control can best be implemented.

For optimal wave-type control, it is advantageous if it is provided that while a first electrode pair is being powered down gradually, the next, adjacent electrode pair is being powered up with regard to intensity. During powering-down, the next, adjacent electrode pair is powered up gradually. When this electrode pair is being powered down gradually, the next adjacent electrode pair is being powered up gradually, and so on. Therefore a kind of wave runs through the apparatus, with regard to the intensity of electrostimulation.

For a further improvement in electrostimulation, it is advantageous if it is provided that the electrode pairs are powered up and down gradually in one or more waves, with regard to intensity.

According to a particularly advantageous embodiment of the invention, it is provided that stimulation is carried out with a current having a low frequency from 0 to 1,000 hertz (Hz) or a medium frequency from one to ten kilohertz (kHz). This range is particularly advantageous for muscle stimulation.

For optimized stimulation, it is provided that the apparatus is heated. In this way, the muscles relax and electrostimulation is particularly effective.

The electrodes can be controlled in pairs, in other words, the electrodes that are disposed on the two sides of the center longitudinal axis, in each instance, or electrode pairs that are disposed merely on the right or left of the center longitudinal axis. However, it is also possible to control all the electrodes individually.

The method according to the invention can be carried out with an apparatus according to the invention, and vice versa.

BRIEF DESCRIPTION OF THE DRAWINGS

Further characteristics and advantages of the invention are evident from the related drawing, in which an exemplary embodiment of the apparatus according to the invention is shown only as an example. The drawing shows.

DETAILED DESCRIPTION OF PREFERRED EMBODIMENTS

Figure 1:
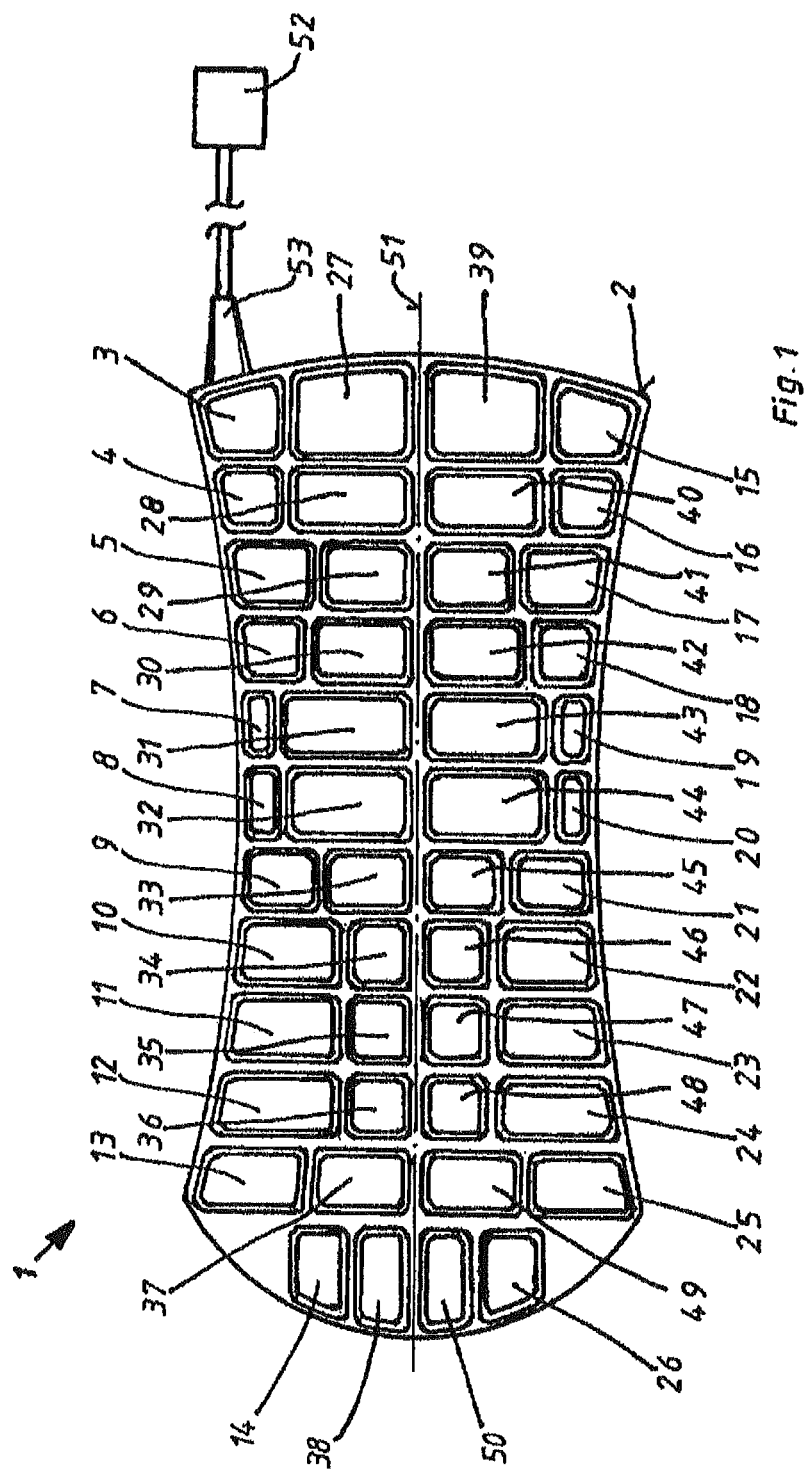
FIG. 1 shows an apparatus according to the invention in a top view.
Figure 2:
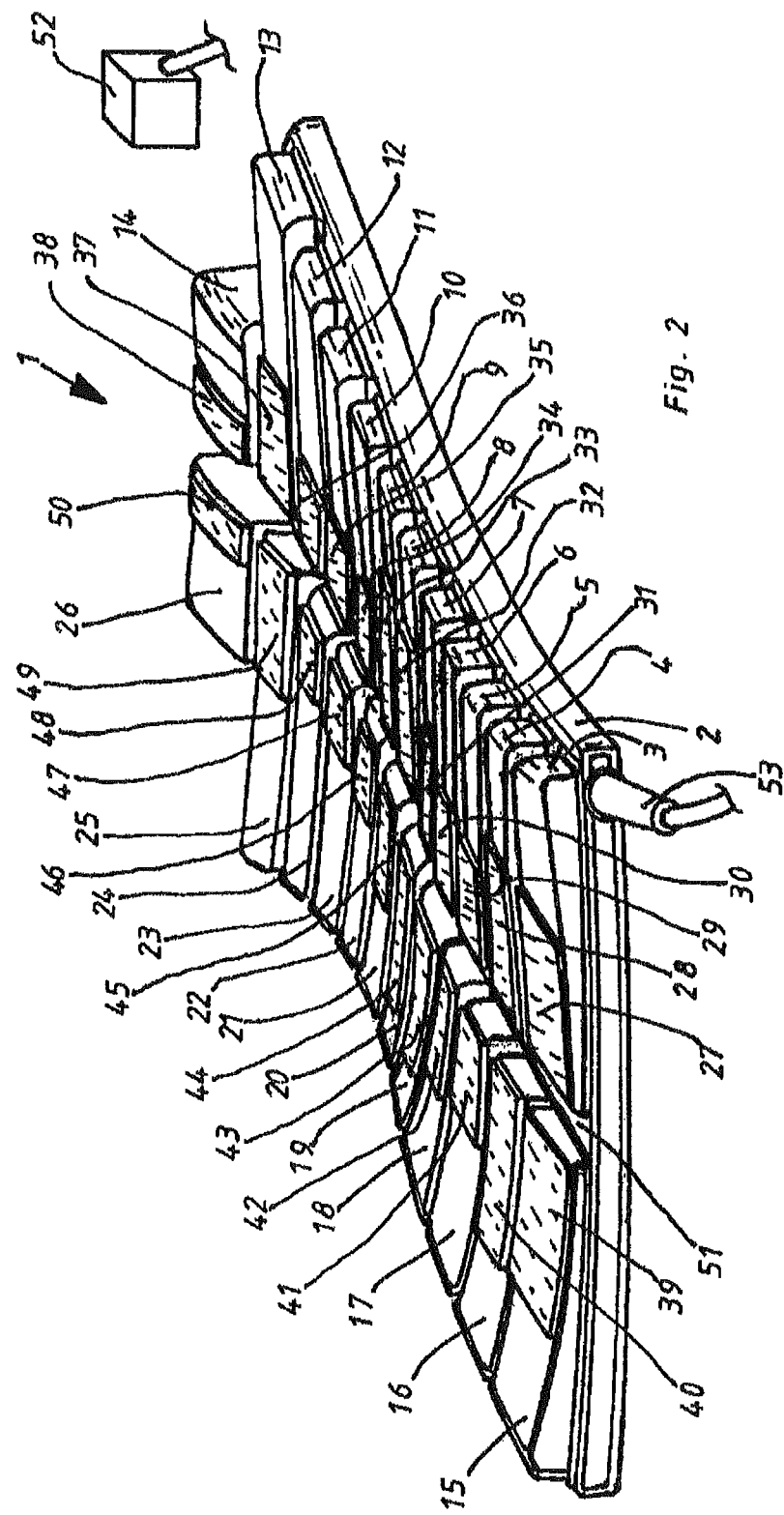
FIG. 2 shows an apparatus according to the invention in a perspective view.
Figure 3:
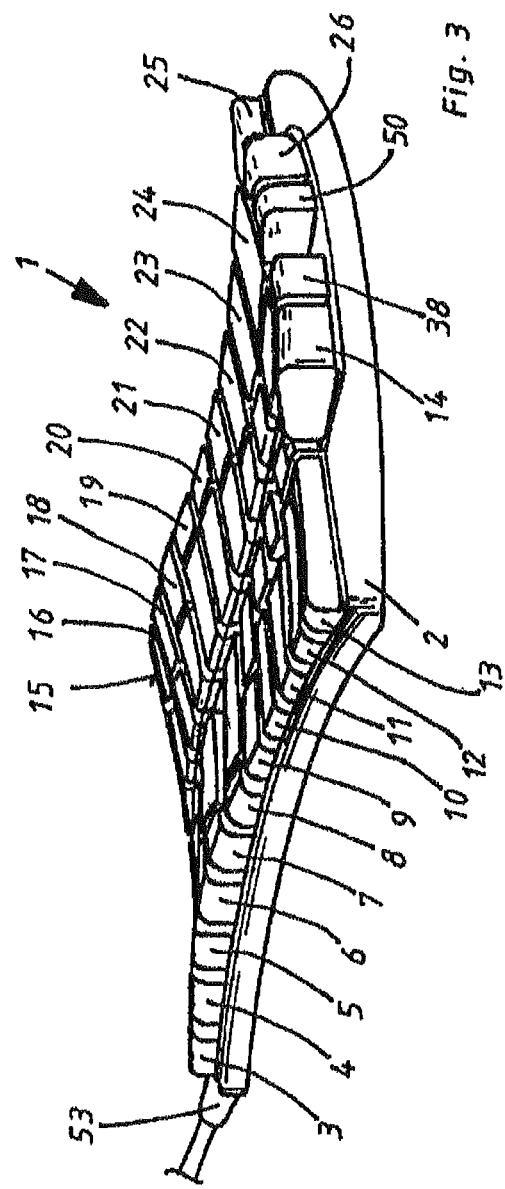
FIG. 3 shows an apparatus according to the invention in a side view.

FIGS. 1 to 3 show an apparatus 1, which has a frame 2 and individual supports 3 to 26. An electrode 27 to 50 is disposed in each individual support 3 to 26.

The apparatus 1 has a center longitudinal axis 51. The apparatus 1 has a recess lying in the center longitudinal axis 51, in other words no contact surface for body parts is provided here.

The couch surface that is formed by the individual supports 3 to 26 is configured to be adapted to a body contour.

In this connection, the individual supports 14, 26 serve for supporting the neck/cervical vertebrae region and the individual supports 3, 15 serve to support the hip region.

The individual supports 3 to 26 are configured transversely, in other words at a 90° angle relative to the center longitudinal axis 51, with recesses lying between them. In this way, it is possible that the entire couch surface optimally adapts to a body, so that the electrodes 27 to 50 have a maximal contact surface with the body (not shown).

The electrodes 27, 39; 28, 40; 29, 41; 30, 42; 31, 43; 32, 44; 33, 45; 34, 46; 35, 47; 36, 48; 37, 49; 38, 50 form pairs, in each instance, which can also be controlled in pairs by a control apparatus 52, using control electronics.

It is also possible to power on the electrodes 39, 40, 41, 42, 43, 44, 45, 46, 47, 48, 49, 50 on one side of the apparatus, for example in the wave form described, without the electrodes 27, 28, 29, 30, 31, 32, 33, 34, 35, 36, 37, 38 on the other side of the center longitudinal axis 51 being turned on.

Control of the electrode pairs 27, 39; 28, 40; 29, 41; 30, 42; 31, 43; 32, 44; 33, 45; 34, 46; 35, 47; 36, 48; 37, 49; 38, 50 can take place as follows:

The electrodes 27, 39 are controlled to be powered up gradually and powered down again gradually. During powering-down, the adjacent electrodes 28, 40 are controlled to be powered up gradually. While the electrodes 28, 40 are controlled to be powered down again gradually, the electrodes 29, 41 are controlled to be powered up gradually, and so on. This method of procedure forms a stimulation wave in the apparatus 1, with which the body (not shown) is stimulated.

During powering up or down of the electrodes 27, 39; 28, 40, no further electrode pairs are powered up or down, so that a single wave passes through the apparatus 1.

However, it is also possible that when the stimulation wave has passed through all the way to the electrode pairs 36, 48; 37, 49, the next wave starts in the electrode pairs 27, 39; 28, 40, so that in this case, two stimulation waves pass through the apparatus 1.

It is also possible that even more waves pass through the apparatus 1 simultaneously.

Control takes place by means of the control apparatus 52, which is shown merely schematically.

The individual supports 3 to 26 can be heated.

It is advantageous if the individual supports 3 to 26 and the frame 2 are formed from silicone.

However, it is also possible to provide other materials.

The electrodes 27, 28, 39, 40 lie in the sacrum region.

The electrodes 29, 41 are disposed in the sacrum region and the lower lumbar vertebrae region, respectively. The lumber vertebrae region extends over the electrodes 30, 31, 32, 42, 43, 44. The electrodes 33, 34, 35, 36, 45, 46, 47, 48 are part of the thoracic vertebrae region. The electrodes 37, 49 are disposed in the shoulder region and the start of the cervical vertebrae region. The electrodes 38, 50 belong to the cervical vertebrae region.

The electrodes 27, 28, 39, 40 in the sacrum region and the electrodes 31, 32, 43, 44 in the lumbar vertebrae region have the greatest width, in other words the greatest expanse from the center longitudinal axis, proceeding at a 90° angle.

The electrodes 38, 50 in the cervical vertebrae region have the smallest width. However, these electrodes 38, 50 are configured to be longer than the other electrodes 27 to 37, 39 to 49 with regard to the direction of the center longitudinal axis 51. The electrodes 33, 34, 35, 36, 45, 46, 47, 48 in the thoracic vertebrae region are wider than the electrodes 38, 50 in the cervical vertebrae region. However, these electrodes 33, 34, 35, 36, 45, 46, 47, 48 in the thoracic vertebrae region are narrower than the other electrodes outside of the cervical vertebrae region.

The apparatus 1 has a connector 53 for a cable (shown discontinuously), by way of which the electrodes 27 to 50 are supplied with current and controlled by the control apparatus 52.

REFERENCE NUMBERS

1 apparatus
2 frame
3 to 26 individual supports
27 to 50 electrodes
51 center longitudinal axis
52 control apparatus
53 cable connector

What is claimed is:

1. An electrostimulation apparatus for electrostimulation, comprising a support comprising a member configured for allowing positioning and support for at least part of the human body to the electrostimulation apparatus, and electrodes disposed in the support, wherein the electrodes are disposed in pairs, relative to a center longitudinal axis of the electrostimulation apparatus, wherein the electrodes are configured to be planar, wherein electrode pairs that are formed from adjacent electrodes are configured so that they can be powered up one after the other or simultaneously, and wherein the apparatus has an interrupted surface having a contour shape that supports the part of the human body for stimulation.

2. The electrostimulation apparatus according to claim 1, wherein two electrodes, in each instance, are disposed in pairs relative to the center longitudinal axis of the apparatus.

3. The electrostimulation apparatus according to claim 1, wherein at least a part of the electrodes has a curved surface.

4. The electrostimulation apparatus according to claim 3, wherein the curved surface of the electrodes is configured as a curved surface adapted to a human body contour and/or wherein the inclination of the electrodes is configured as an inclination adapted to a human body contour.

5. The electrostimulation apparatus according to claim 1, wherein at least a part of the electrodes is disposed inclined relative to a base surface of the support.

6. The electrostimulation apparatus according to claim 1, wherein at least six electrode pairs are provided.

7. The electrostimulation apparatus according to claim 1, wherein at least twelve electrode pairs are provided.

8. The electrostimulation apparatus according to claim 1, wherein the electrode pairs are configured so that they can be controlled in wave form, one after the other.

9. The electrostimulation apparatus according to claim 1, wherein the electrode pairs are configured so that they can be powered up gradually and powered down again gradually.

10. The electrostimulation apparatus according to claim 1, wherein during gradual powering down of a preceding electrode pair gradual powering up of the next, adjacent electrode pair is provided.

11. The electrostimulation apparatus according to claim 1, wherein the electrode pairs are configured so that they can be powered up gradually and powered down again gradually, in one or more waves.

12. The electrostimulation apparatus according to claim 1, wherein stimulation is carried out with a current having a low frequency between 0 and 1,000 hertz (Hz) or a medium frequency between one and ten kilohertz (kHz).

13. The electrostimulation apparatus according to claim 12, wherein the electrostimulation apparatus has at least two individual supports.

14. The electrostimulation apparatus according to claim 12, wherein the electrostimulation apparatus has at least one electrode, in each instance, in each individual support.

15. The electrostimulation apparatus according to claim 1, wherein the electrostimulation apparatus is configured so that it can be heated.

16. The electrostimulation apparatus according to claim 1, wherein a base body of the electrostimulation apparatus is formed from silicone.

17. The electrostimulation apparatus according to claim 1, wherein the interrupted surface has a continuous recess in the center longitudinal axis.

18. The electrostimulation apparatus according to claim 17, wherein the electrodes are disposed bordering on the recess disposed in the center longitudinal axis.

19. The electrostimulation apparatus according to claim 1, wherein the electrodes have different sizes, at least in part, with regard to their contact surface.

20. The electrostimulation apparatus according to claim 1, wherein the electrodes are configured so that they can be controlled individually with regard to the stimulation intensity.

21. A method for controlling multiple electrodes in an electrostimulation apparatus for electrostimulation, wherein the electrodes are disposed in or on the electrostimulation apparatus, which has a support comprising a member configured for allowing positioning and support for at least part of the human body to the electrostimulation apparatus, wherein the electrodes are configured so that they can be powered up one after the other or simultaneously, wherein the electrodes are powered up individually or in pairs, with regard to a duration and/or an intensity of the stimulation, and wherein the electrostimulation apparatus has an interrupted surface having a contour shape that supports the part of the human body for stimulation.

22. The method according to claim 21, wherein the electrodes or electrode pairs are controlled in wave form, one after the other, with regard to intensity.

23. The method according to claim 21, wherein the electrodes or electrode pairs are configured so that they can be powered up gradually and powered down again gradually, with regard to intensity.

24. The method according to claim 21, wherein while a first electrode pair is gradually powering down, the next, adjacent electrode pair is gradually powering up, in terms of intensity.

25. The method according to claim 21, wherein the electrode pairs are controlled in one or more waves, with regard to intensity, gradually powering up and gradually powering down.

26. The method according to claim 21, wherein stimulation is carried out with a current having a low frequency between 0 and 1,000 hertz (Hz) or a medium frequency between one and ten kilohertz (kHz).

27. The method according to claim 21, wherein the electrostimulation apparatus is heated.

28. The method according to claim 21, wherein the electrodes are disposed in the support, wherein the electrodes are disposed in pairs, relative to a center longitudinal axis of the electrostimulation apparatus, wherein the electrodes are configured to be planar, and wherein the electrode pairs that are formed from adjacent electrodes are configured so that they can be powered up one after the other or simultaneously.

\* \* \* \* \*